US006746843B2

(12) United States Patent
Alexander et al.

(10) Patent No.: US 6,746,843 B2
(45) Date of Patent: Jun. 8, 2004

(54) METHODS OF SCREENING NOVEL AGENTS FOR USE IN CANCER THERAPY AND PREVENTION

(75) Inventors: Hannah Alexander, Columbia, MO (US); Stephen Alexander, Columbia, MO (US)

(73) Assignee: The Curators of The University of Missouri, Columbia, MO (US)

( * ) Notice: Subject to any disclaimer, the term of this patent is extended or adjusted under 35 U.S.C. 154(b) by 66 days.

(21) Appl. No.: 09/915,225

(22) Filed: Jul. 25, 2001

(65) Prior Publication Data

US 2002/0042044 A1 Apr. 11, 2002

Related U.S. Application Data

(60) Provisional application No. 60/221,908, filed on Jul. 31, 2000.

(51) Int. Cl.[7] .................................................. C12Q 1/68

(52) U.S. Cl. ............................ 435/6; 435/29; 435/32; 435/254.11; 435/483; 435/484

(58) Field of Search ........................... 435/4, 29, 32, 435/41, 243, 6, 254.11, 483, 484

(56) References Cited

PUBLICATIONS

Broughton et al., "Molecular and cellular analysis of the DNA repair defect in a patient in Xeroderma Pigmentosum complementation group D who has the clinical features of Xeroderma Pigmentosum and Cockayne Syndrome," *Am. J. Hum. Genet.*, 56:167–174, 1995.
Deering, R., "DNA repair in *Dicytostelium*," *Dev. Genet.* 9:483–493, 1988.
Drapkin et al., "Dual role of the TFIIH in DNA excision repair and in transcription by RNA polymerase II," *Nature*, 368:769–722, 1994.
Freeland et al., "Apurinic/apyrimidinic (AP) endonuclease from *Dictyostelium discoideum*: cloning, nucleotide sequence and induction by sublethal levels of DNA damaging agents," *Nucl. Acid Res.* 24:1950–1953,1996.
Friedberg et al., *DNA Repair and Mutagenesis*, ASM Press, Washington, DC, 1995.
Friedberg, "Relationships between DNA repair and transcription," *Annu. Rev. Biochem.*, 65:15–42, 1996.
Garcia et al., "Differential developmental expression and cell type specificity of *Dictyostelium* catalases and their response to oxidative stress and UV–light," *Biochim. Biophys. Acta* 1492:295–310, 2000.
Gulyas and Donahue, "SSL2, a suppressor of a stem–loop mutation in the HIS4 leader encodes the yeast homolog of human ERCC–3," *Cell*, 69:1031–1042, 1992.
Guzder et al., "Lethality in yeast of Trichothiodystrophy (TTD) mutations in the human Xeroderma Pigmentosum Group D Gene," *J. Biol. Chem.*, 270:17660–17663, 1995.

Guzder et al., "RAD25 is a DNA helicase required for DNA repair and RNA polymerase II transcription," *Nature*, 369:578–581, 1994.
Hanawalt and Mellon, "Stranded in an active gene," *Curr. Biol.*, 3:67–69, 1993.
Hanawalt, "Transcription–coupled repair and human disease," *Science*, 266:1957–1958, 1994.
Higgins et al., "Isolation and characterization of the RAD3 gene Saccharomyces cerevisiae and inviability of rad3 deletion mutants," *Proc. Nat'l Acad. Sci. USA*, 80:5680–5684, 1983.
Kessin, *Dictyostelium*:Evolution, Cell Biology and Development of Multicellularity, Cambridge University Press, Cambridge, UK and New York, 2000.
Kraemer et al., "Xeroderma Pigmentosum and related disorders: examining the linkage between defective DNA repair and cancer," *J. Invest. Dermatol.*, 103:96S–101S, 1994.
Kuspa and Loomis, "Tagging developmental genes in *Dictyostelium* by restriction enzyme–mediated integration of plasmid DNA," *Proc. Nat'l Acad. Sci. USA* 89:8803–8807, 1992.
Kuspa and Loomis, "Transformation of Dictyostelium: Gene disruptions, insertional mutagenesis, and promoter traps," *Methods in Molecular Genetics*, 3:3–21, 1994.
Lee et al., "Differential developmental expression of the repB and repD Xeroderma pigmentosum related DNA helicase genes from Dictyostelium discoideum," *Nucl. Acids Res.* 25(12):2365–2374, 1997.
Lehmann, "Nucleotide excision repair and the link with transcription," *Trends Biochem. Sci.*, 20:402–405, 1995.
Li et al., "Molecular basis for resistance to the anticancer drug cisplatin in Dictyostelium," *Microbiology*, 146:2219–2227,2000.
Loomis, *The Development of Dictyostelium discoideum*. Academic Press, New York, 1982.
Park et al., "RAD25 (SSL2), the yeast homolog of the human xeroderma pigmentosum group B DNA repair gene, is essential for viability," *Proc. Nat'l Acad. Sci. USA*, 89:11461–11420, 1992.
Sancar, "DNA excision repair," *Annu. Rev. Biochem.*, 65:43–81, 1996.
Sussman, "Cultivation and synchronus morphogenesis of *Dictyostelium* under controlled experimental conditions," *Meth. Cell Biol.* 28:9–29, 1987.

(List continued on next page.)

Primary Examiner—James Ketter
(74) Attorney, Agent, or Firm—Fulbright & Jaworski LLP

(57) ABSTRACT

The present invention provides for methods of screening agents for cancer therapeutic and prophylactic activity. In particular embodiments, cells of the cellular slime mold *Dictyostelium discoideum* are contacted with candidate agents and the expression of genes in the Nucleotide Excision Repair (NER) and Base Excision Repair (BER) pathways are examined. Such genes include the helicases repB and repD, and the apurinic-apyrmidinic endonuclease APE.

31 Claims, No Drawings

OTHER PUBLICATIONS

Svejstrup et al., "Different forms of TFIIH for transcription and DNA repair: Holo–TFIIH and a nucleotide excision repairosome," *Cell,* 80:21–28, 1995.

Sweder and Hanawalt, "The COOH terminus of suppressor of stem loop (SSL2/RAD25) in yeast is essential for overall genomic excision repair and transcription–coupled repair," *J. Biol. Chem.,* 269:1852–1857, 1994.

Takayama et al., "Defects in the DNA repair and transcription gene ERCC2 in the cancer–prone disorder Xeroderma Pigmentosum Group D," *Cancer Res.,* 55:5656–5663, 1995.

Van Vuuren et al., "Correction of xeroderma pigmentosum repair defect by basal transcription factor BTF2 (TFIIH)," *EMBO J.,* 13(7):1645–1653,1994.

Yu et al., "Rapid changes of Nucleotide excision gene expression following UV–irradiation and cisplatin treatment Of *Dictyostelium Discoideum,*" *Nucl. Acids Res.,* 26(14):3397–3403, 1998.

METHODS OF SCREENING NOVEL AGENTS FOR USE IN CANCER THERAPY AND PREVENTION

This application claims benefit of priority to U.S. Provisional Application Serial No. 60/221,908, having a priority date of Jul. 31, 2000.

The government owns rights in the present invention pursuant to grant number GM53929 from the National Institutes of Health.

BACKGROUND OF THE INVENTION

1. Field of the Invention

The present invention relates generally to the fields of cell biology, molecular biology and oncology. More particularly, it concerns the use of *Dictyostelium discoideum* cells in the screening of chemical agents for use in cancer therapy and cancer prevention.

2. Description of Related Art

Cells are continually exposed to a variety of extracellular insults that can damage their DNA, such as UV light, ionizing radiation and chemicals. DNA damage can lead to mutations and ultimately cancer. It is ironic that the radio- and chemotherapies that are used to treat many malignancies will eventually result in the selection of resistant tumor cells, or will cause secondary tumors by virtue of their DNA damaging capacity. Clearly, a full understanding of the mechanisms of DNA damage, DNA repair and drug resistance is essential for the effective prevention and treatment of cancer.

All species have mechanisms for repairing DNA damage. These mechanisms are highly specific, and allow the cell to recognize a specific type of damage and mount an appropriate response. Moreover, these systems are highly conserved throughout species, and information that is obtained from studying model organisms is relevant to humans.

SUMMARY OF THE INVENTION

Thus, in accordance with the present invention, there is provided a method of screening agents for use in the prevention or treatment of cancer comprising (a) contacting a vegetative cell of *Dictyostelium discoideum* with a test agent; (b) assessing the cytotoxicity of said test agent; (c) assessing the effect of said test agent on the expression of one or more of repB, repD and APE gene products; and (d) comparing said cytotoxicity and said expression in the presence of said test agent with a vegetative cell of *Dictyostelium discoideum* not exposed to said test agent; wherein (i) a test agent that is cytotoxic but does not induce expression of one or more of repB, repD and APE gene products will be useful as a chemotherapeutic; (ii) a test agent that is not cytotoxic but does induce expression of one or more of repB, repD and APE gene products will be useful as a chemopreventative; and (iii) a test agent that inhibits the expression of one or more of repB, repD and APE gene products will be useful as a chemotherapeutic when applied in combination with a DNA damaging agent.

Assessing expression may comprise assessing repB expression, assessing repD expression, assessing APE expression, assessing repB and repD expression, assessing repB and APE expression, assessing repD and APE, or assessing repB, repD and APE expression. In an additional step, one may measure, in a vegetative cell of *Dictyostelium discoideum* not treated with said test agent, the expression of the same gene or genes as set forth above.

Cytoxocity may be assessed by measuring viability by clonal plating, trypan blue exclusion, phyloxine B dye exclusion, and degradation/laddering of DNA. Expression may be assessed by hybridization of a probe to a target nucleic acid, including RT-PCR™ and "real time" PCR™. One or more probes may comprise a label, such as a radiolabel, a fluorophore label, a chemilluminescent label, an enzyme label or a ligand (such as biotin, where the ligand is detected by contacting with enzyme-conjugated avidin or streptavidin and a detectable enzyme substrate). The method may also comprise binding target nucleic acid to a substrate, such as a nylon or nitrocellulose membrane.

Expression also may be assessed by means of an expression cassette stably transformed into said a vegetative cell of *Dictyostelium discoideum*, said expression cassette comprising a nucleic acid segment encoding a detectable reporter enzyme under the transcriptional control of a repB, repD or APE promoter region. The detectable reporter enzyme may encode $\beta$-galactosidase, $\beta$-glucuronidase, luciferase or green fluorescent protein.

The assay may further comprise a positive control for inhibition of expression of one or more of repB, repD and APE gene products, a positive control for induction of expression of one or more of repB, repD and APE gene products, and/or a positive control for cytotoxicity.

The assay may further comprise a negative control for inhibition of expression of one or more of repB, repD and APE gene products, a negative control for induction of expression of one or more of repB, repD and APE gene products, and/or a negative control for cytotoxicity.

The test agent may be a naturally-occurring molecule, a synthetic molecule, or a synthetic derivative of a naturally-occurring molecule. The method also may further comprise assessing DNA damage in said cell, for example, by mass spectroscopy.

In another embodiment, there is provided a vegetative cell of *Dictyostelium discoideum* stably transformed with an expression cassette comprising a nucleic acid segment encoding a detectable reporter enzyme under the transcriptional control of a repB, repD or APE promoter region.

In still yet another embodiment, there is provided a method of making a compound for use in the prevention or treatment of cancer comprising (a) contacting a vegetative cell of *Dictyostelium discoideum* with said compound; (b) assessing the cytotoxicity of said compound; (c) assessing the effect of said compound on the expression of one or more of repB, repD and APE; (d) comparing said cytotoxicity and said expression in the presence of said compound with a vegetative cell of *Dictyostelium discoideum* not exposed to said compound; and (e) making said compound.

DESCRIPTION OF ILLUSTRATIVE EMBODIMENTS

Cancer is a leading cause of mortality in both industrialized and non-industrialized countries, with over one million new cases identified each year in the U.S. alone. Progress has been made in the identification of new drugs that, alone or in combination, work to inhibit cancer cells. However, tumors frequently become resistant to chemotherapeutic drugs. Thus, there is a constant need to identify new and more powerful drugs for use in cancer therapy.

1. The Present Invention

The cellular slime mold *Dictyostelium discoideum* offers an amenable system for the analysis of the cellular response to chemotherapeutic drugs. Although a relatively simple haploid organism, this organism exhibits many of the aspects of cellular physiology and development seen in more complex organisms, thus allowing the study of complicated genetic responses that would be impossible using higher organisms. The present inventors propose to utilize their knowledge of Dictyostelium molecular biology to created screening assays for agents that can be used against cancers as well as benign hyperproliferative diseases.

The assays will focus on the expression of two different genes in the Nucleotide Excision Repair (NER) pathway—repB, repD—and the Base Excision Repair (BER) gene APE. The expression of these genes will be correlated to the cytotoxcity of the agent. Three different outcomes for the assays are envisioned:

compounds that are cytotoxic but do not induce expression of repB, repD or APE: compounds will be useful as anticancer drugs because they do not induce expression of repair genes;

compounds that are not cytotoxic but induce expression of repB, repD or APE: compounds of this class will be anti-cancer drug candidates used to prevent cancer by inducing DNA repair; and compounds that suppress the expression of repB, repD or APE: compounds of this class would preferentially effect rapidly growing cells, and would render them more susceptible to DNA damaging agents The exploitation of this assay is described in detail in the following pages.

2. *Dictyostelium discoideum*

Dictyostelium is a relatively simple eukaryotic organism, but exhibits cellular and developmental properties of higher multicellular organisms. There is a high degree of evolutionary conservation of individual proteins, enzymes and biochemical pathways, including DNA replication and cell cycle control between Dictyostelium and humans. It has a relatively small genome (35 mb), and like human cells, has a plasma membrane and no cell wall. The ease with which it can be manipulated experimentally has made it a favorite organism for cell and developmental biology studies.

Dictyostelium is unicellular and haploid (which facilitates genetic analysis). The single cells are cultured in liquid medium and divide mitotically. This mitotic growth can proceed indefinitely, without ever entering the developmental phase, as long as there is adequate nutrient supply. If the food source is exhausted or removed, the cells begin a multicellular developmental cycle that ends in the formation of environmentally resistant spores (Kessin, 2000; Loomis, 1982). It should be noted that growth and development are mutually exclusive in this organism, and that this invention will be practiced on logarithmically-dividing single cells.

Hundreds of Dictyostelium genes and their products have been studied in detail. Genome projects have already identified three-fourths of the estimated 14,000 genes, and cDNA's are readily available. Dictyostelium has been particularly useful in studying the signal transduction mechanisms controlling how cells move towards chemoattractants, the cytoskeletal mechanics responsible for cell movement, cytokinesis, the mechanisms underlying endocytosis, and regulated protein secretion. Standard procedures exist for gene deletion, exchange and overexpression, as well as the Restriction Enzyme Mediated Insertion method for insertional mutagenesis, which allows for the identification of the affected gene in the mutant. Standard methods cell growth, storage and determination of viability are well described (Kuspa and Loomis, 1987; Garcia et al., 2000; Sussman, 1987).

A number of studies provide a fundamental picture of DNA repair in mitotically dividing Dictyostelium cells. They generated a series of mutants which displayed varying degrees of increased sensitivity to γ-irradiation, and parasexual genetic analyses placed these mutations into 11 complementation groups. However, due to the lack of a system for molecular complementation in *Dictyostelium discoideum* at the time, none of the mutated genes were identified. These γ-irradiation sensitive mutants often also displayed parallel sensitivity to UV-irradiation and other DNA damaging chemical such as 4-NQO (4-nitroquinoline-1-oxide) and bleomycin, but again, the molecular basis for this cross-resistance is not yet understood (Deering, 1988).

3. Nucleotide and Base Excision Repair Genes as Molecular Targets for Screening

Nucleotide Excision Repair (NER) is an important cellular defense mechanism, which protects the integrity of the genome by removing DNA damage caused by UV light or chemical agents. NER is a multistep pathway, and defects in the individual components of this pathway result in impaired DNA repair and increased sensitivity to UV (Sancar, 1996). Cell fusion experiments have identified eight complementation groups (XP-A-G and a variant group XP-V). Most of these complementation groups have been correlated with specific loci in the NER pathway, and the corresponding genes for most of these groups have been cloned. In general, these genes exhibit a very high degree of conservation across species, although interspecies complementation is limited, implying that the specific protein—protein interactions necessary for NER are unique to each organism (Kraemer et al., 1994; Friedberg et al., 1995).

NER preferentially occurs on the template strand of actively transcribed genes (Hanawalt, 1994; Hanawalt & Mellon, 1993). This mechanistic relation between transcription and repair is a result of the fact that the transcription initiation complex holo-TFIIH and the repair complex (repairo-some) share a common six polypeptide core, the TFIIH-core (Drapkin et al., 1994; Sweder & Hanawal, 1994; Svejstrup et al., 1995; Van Vuuren et al., 1994). The current notion is that when transcription is stalled at a site of damage, coupling factors with high affinity for the stalled elongation complex recruit the repair complex. When the repair is accomplished, the TFIIH-core then becomes part of the initiation complex to restart transcription (Friedberg, 1996).

XPB and XPD are the homologs of the yeast RAD25/SSL2 (Park et al., 1992; Gulyas and Donahue, 1992) and RAD3 (Higgins et al., 1983) genes, respectively. Both genes encode DNA helicases of the SF2 superfamily. The XPB protein functions in the 3'–>5' direction and the XPD functions 5'–>3'. Both these polypeptides are part of the common TFIIH core and both have been shown to participate in both RNA polymerase II mediated transcription and NER (Drapkin et al., 1994; Van Vuuren et al., 1994; Guzder et al., 1994; 1995). Mutations in XPB and XPD can result in diverse clinical phenotypes of either XP alone, or combined XP/CS (cockayne's syndrome) or XP/TTD (trichothiodystrophy), depending on what functional domain of the polypeptide is altered (Broughton et al., 1995; Lehmann, 1995; Takayama et al., 1995). It is possible that changes in these transcription related genes, in turn, lead to alteration of the rate and/or extent of expression of a particular subset of downstream genes that are critical for specific stages in development.

Base Excision Repair (BER) is also a multi-step pathway, initiated by DNA glycosylase enzymes. These enzymes modify bases on DNA to generate sites of base loss, call apurinic or apyrimidinic (AP) sites. These AP sites serve, in turn, as substrates for apurinic/apyrimidinic endonucleases, which generate incisions or nicks in the DNA, thus preparing the DNA for subsequent excision of the damage, and eventual repair by DNA polymerase and DNA ligase.

The present inventors have determined that certain NER- and BER-related genes in Dictyostelium maybe used as targets in screening assays for potential anti-cancer drugs. These genes include repB and repD, which are homologs of the XPB and XPD DNA helicases (Lee et al., 1997a), and APE, which is a apurinic/apyrimidinic endonuclease (Freeland et al., 1996). By assessing changes in the expression of these gene products, or the expression of screenable markers under control of the related repB, repD and APE promoters, induced by candidate substances, and correlate these changes in expression of the screenable markers to the cytotoxicity of the substances, one can determine which of the outcomes described above is the result of exposure to each candidate substance, and therefore determine the potential use of the agent in cancer chemotherapy and chemoprevention.

A. RepB/RepD

The Dictyostelium repB (GenBank U77065) and repD (GenBank U77066) genes were first reported by the inventors (Lee et al., 1997a), and were identified by hybridization with the yeast RAD25 and RAD3 genes, respectively. A 3.7 kb BglII-ClaI fragment for repB (pSKSL5) and a 4.3 kb ClaI-PstI fragment for repD (pSKSL11) were cloned from sucrose gradient fractionated DNA.

repB. A 3093 bp sequence was cloned surrounding the repB gene. The genomic clone is 2578 bp long, and contains one 175 bp intron at position 125–299, as was determined by comparing the genomic sequence to the cDNA sequence obtained by RT-PCR™. repB was mapped to chromosome 3 of the Dictyostelium genome. Sequencing revealed a few putative TATA sequences in the 5' untranslated region, as well as multiple AAUAAA polyadenylation sites on the 3' end. The two exons encode a putative 90 kDa polypeptide which shares homology with the human XPB (54%), the Saccharomyces cerevisiae Rad25 (53%), the Drosophila Haywire (51%) and the arabidopsis XPBara (60%) proteins.

repD. 2762 bp surrounding the repD region has been sequenced. The gene contains no introns and has been mapped to chromosome 1 of Dictyostelium. The 2331 bp open reading frame encodes a 88 kDa predicted polypeptide. The putative RepD protein shares homology with the human XPD (54%), the S. cerevisiae Rad3 (50%), the S. pombe rhp3 (50%), the Chinese hamster Excision Repair Cross Complementing 2 (ERCC2) (53%) and the fish X. maculatus XPD (52%) proteins.

Both the predicted repB and repD proteins contain all seven conserved helicase domains. There is very high homology between the RepB and RepD proteins and their yeast and mammalian counterparts within all of these domains, and most notably in regions I and II, which are the A and B motifs of the Walker 'type-A' consensus sequences (Gorbalenya and Koonin, 1993; Lohman and Bjornson, 1996). The NTP (nucleotide triphosphate) binding site in region I contains GAGKS/T in all four XPB related proteins, and GTGKT in all XPD related proteins. The $Mg^{++}$ binding site in region II contains DEVH in all XPB related proteins and DEAH in all XPD related proteins. These results indicate that both proteins are members of the subgroup of the DExH containing proteins in the SF2 superfamily of helicases. In addition, the RepB protein exhibits high sequence conservation in other identified domains of the XPB/RAD25 proteins, namely, a putative nuclear localization site on the N-terminus of the protein, a DNA binding domain and three acidic domains.

B. APE

Sequencing of a Dictyostelium cDNA (GenBank U31631; Freeland et al., 1996) containing the APE gene revealed an open reading frame from bases 1842 to 2924. The agreement of the coding sequence from the genomic DNA and the cDNA from 1836 to 2061 revealed no introns in the 5' portion of the gene. The sequence predicts a protein of 361 amino acids, with a molecular weight of 41,225 Da. The predicted amino acid sequence shows high homology with the major human/E. coli exonuclease family of AP endonucleases. For example, there is 47% identity and 64% similarity to the APE endonuclease of human cells (also called REF1) using the C-terminal 257 amino acids of the Dictyostelium protein. The 104 amino acids at the N-terminus show only low homology with other AP endonucleases. However, amino acids 50–80 have 75% structural similarity to amino acids 170–200 of the high mobility group 1 (HMG) chromatin protein from various species. Amino acids 20–80 have 65% similarity to amino acids 190–250 of many nucleolins. It has been suggested that the glutamate-rich domain functions as a nuclear transport factor or as a non-specific interaction site for DNA binding proteins. A short potential nuclear localization signal, KKRK, is also noted at amino acids 41–44. Although no direct evidence exists, it has been argued that these N-terminal domains allow the inference that nuclear localization of APE occurs.

C. Effect of DNA Damage on Gene Expression

Exposing Dictyostelium cells to UV results in loss of viability. Moreover, the expression of the rep genes is affected by exposing the cells to UV light. When logarithmically growing cells are treated with different fluences, the changes in NER gene expression are rapid, dose dependent, and transient. In the case of the repB and repD genes, the inventors have shown that the levels of cognate mRNA increases from basal levels within 10 minutes, reaching a peak within an hour and then rapidly decreasing back to the basal level by two hours (Yu et al., 1998). Similar findings of UV inducibility in Dictyostelium have been reported for apurinic/apyrimidinic endonulcease genes (Freeland et al., 1996)

This study was extended to the effects of cisplatin (Yu et al., 1998). At 300 $\mu M$ cisplatin the viability of the cells is reduced by three orders of magnitude. As with UV, the levels of repB and repD mRNAs rapidly increase from basal levels after cisplatin treatment. The inventors have hypothesized that the ability to rapidly modulate these genes, as well as other genes involved in NER, is at least partially responsible for the resistance of Dictyostelium to DNA damage by UV and chemicals.

4. Screening Assays

Thus, in accordance with the present invention, methods are provided for identifying agents that do or do not alter the expression of repB, repD and/or APE genes and that are or are not cytotoxic to cells of Dictyostelium discoideum. These assays may comprise random screening of large libraries of candidate substances; alternatively, the assays may be used to focus on particular classes of compounds selected with an eye towards structural attributes that are believed to make them DNA damaging and/or cytotoxic, but not limited to these characteristics.

To identify a potential chemotherapeutic or chemopreventative agent, one generally will determine the level of expression of repB, repD and/or APE and determine the viability of Dictyostelium discoideum cells in the presence and absence of the candidate agent. For example, a method generally comprises:

(a) providing a candidate agent;
(b) treating an appropriate cell with a candidate agent;
(c) measuring expression of repB, repD and/or APE in the cell of step (b);
(d) comparing the expression of repB, repD and/or APE in step (c) with the expression of repB, repD and/or APE in a cell not treated with the candidate agent; and
(e) determining the cytotoxicity of the candidate agent by evaluating cell viability after treatment of a cell with the candidate agent, where differences between the measured characteristics in the treated and untreated cells indicates that said candidate agent is a potential chemotherapeutic or chemopreventative.

It often is useful to actually perform the control experiment looking for expression of repB, repD and/or APE in the absence of the candidate agent. It will, of course, be understood that all the screening methods of the present invention are useful in themselves notwithstanding the fact that effective candidates may not be found. The invention provides methods for screening for such candidates, not solely methods of finding them.

A negative control for alteration of expression may also prove useful. Such a control would involve assaying the expression of such genes as, for example, actin, discoidin I and alkaline phosphatase. Since these genes have nothing to do with DNA damage or repair, they should not be affected by the test agents.

Another important aspect of the invention is to assay for cytotoxicity. Cell viability assays can be performed in a variety of different ways, for example, clonal plating, trypan blue exclusion, phyloxine B dye exclusion, and degradation/laddering of DNA.

As used herein the term "candidate substance" refers to any molecule that may potentially modulate expression of repB, repD and/or APE. The candidate substance may be any molecule including a protein or fragment thereof, a small molecule, or even a nucleic acid molecule. These can be natural compounds, synthetic compounds or synthetic modifications of natural compounds. "Rational drug design" includes not only comparisons with known inhibitors and activators, but predictions relating to the structure of target molecules. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

One may simply acquire, from various commercial or non-commercial sources, small molecule libraries that are believed to meet the basic criteria for useful drugs in an effort to "brute force" the identification of useful compounds. Screening of such libraries, including combinatorially generated libraries, is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecules or any other compounds that may be designed through rational drug design starting from known inhibitors or stimulators.

5. Detecting Nucleic Acids

In one embodiment, the present invention involves screening for changes in the expression of a target gene by looking at mRNA levels. This will involve one of a number of different procedures, including Northern blotting, quantitative RT-PCR™ or "real-time" PCR™. In their most fundamental aspects, these methods rely on hybridization of a probe sequence to a target sequence. Various aspects of this embodiment are provided below.

A. Hybridization

The use of a probe or primer of between 15 nucleotides or longer in length, allows the formation of a duplex molecule that is both stable and selective. Molecules having complementary sequences over contiguous stretches greater than 20 bases in length are generally preferred, to increase stability and/or selectivity of the hybrid molecules obtained. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as biotin, which are capable of being detected. In preferred embodiments, one may desire to employ a fluorescent label or an enzyme tag such as alkaline phosphatase or peroxidase, instead of radioactive or other environmentally undesirable reagents to detect biotinylated probes. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test RNA or DNA is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells according to standard methodologies (Sambrook et al., 1989). In certain embodiments, analysis is performed on whole cell homogenates without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Primers may be provided in double-stranded and/or single-stranded form, although the single-stranded form is preferred for PCR™.

Pairs of primers designed to selectively hybridize to nucleic acids corresponding to repB, repD and APE are contacted with the template nucleic acid under conditions that permit selective hybridization. Depending upon the desired application, high stringency hybridization conditions may be selected that will only allow hybridization to sequences that are completely complementary to the primers. Once hybridized, the template-primer complex is contacted with one or more polymerases that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label.

Real-time PCR™ amplifies DNA much faster by heating samples using air instead of thermal blocks and by amplifying DNA in a capillary tube with a high surface-to-volume ratio. Real-time PCR™ combines amplification and fluorescence detection in the same instrument, and allows samples to be analyzed after every round of PCR™ amplification. The initial number of target DNA molecules can be determined (quantitatively) through analysis of the kinetics of accumulation of fluorescently-labeled PCR™ product. In addition, the PCR™ products can be characterized by analysis of their melting behavior, thereby allowing differentiation between a specific amplicon and nonspecific DNA fragments. In addition, internal control fragments can be amplified in the same PCR™ reaction as the target gene by using probes, and labeled with different detectable fluorophores specific to the different genes. Three different fragments can be amplified and detected in the same reaction using the LightCycler™ System because this system is capable of reading fluorescence at three different wavelengths (Roche Diagnostic Corporation, Indianapolis, Ind.).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR™ are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid, or by the use of the commercial product GENECLEAN™ (Q-biogene).

Separation of nucleic acids may also be effected by chromatographic techniques known in the art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe can be conjugated to a chromophore but may be radiolabeled. In another embodiment, the probe is conjugated to a binding partner, such as biotin, or another binding partner carrying a detectable moiety.

U.S. Pat. No. 5,279,721, incorporated by reference herein, discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. RNAse Protection

In a certain embodiments, the levels repB, repD and APE can be measured by an RNase protection technique. The DNA probes for repB, repD and APE will be of defined length, for example 300 bp, 360 bp and 420 bp respectively. These probes will be tagged to enable detection (see above). Alternatively, the probes are labeled radioactively by random priming technique (well known in the art, and see Lee et al., 1997a). The probes are hybridized in liquid to the RNA samples being analyzed. Since the probes are of a defined length, and shorter than their cognate RNA molecule, single strands of RNA are left flanking both side of the DNA-RNA duplex. These single stranded stretches of RNA are digested by single strand specific RNase. The RNA-DNA duplex is then denatured by heat, and the DNA fragments are separated on a sequencing gel, capable of separating DNA fragments of the above size. The amount of bound probe is quantified, (for example using a phosphorimager for radioactively labeled probes). The technique is useful in that all three genes (and a negative control) can be run at the same time.

E. Kits

All the essential materials and/or reagents required for detecting targets in a sample may be assembled together in a kit. This generally will comprise a probe or primers designed to hybridize specifically to individual nucleic acids of interest in the practice of the present invention, including repB, repD and APE. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

6. Cells Engineered with Detection Systems

In another embodiment, the present invention involves the use of *Dictyostelium discoideum* cells that have been engineered to express a screenable marker protein. The marker is regulated by an appropriate promoter—in this case from repB, repD or APE. Thus, rather than measuring the expression repB, repD or APE directly, a surrogate for their expression is used. The following provides a discuss of relevant technologies for this embodiment.

A. Screenable Marker Proteins

Screenable marker genes are genes that impart a distinct phenotype to cells expressing the marker gene and thus allow such transformed cells to be distinguished from cells that do not have the marker. In the present invention, these genes would be linked to the appropriate promoter and the expression construct, optionally including other regulatory elements such as polyadenylation sequences, transcription termination sequences, internal ribosome entry sites, enhances and origins of replication, and transferred into host cells.

Screenable markers that may be employed include a β-glucuronidase (GUS), β-galactosidase or green fluorescent protein. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates.

B. Selectable Marker Proteins

In the creation of suitable engineered cells, one may choose to utilize a second marker protein, in this case permitting the selection of the transformed *Dictyostelium discoideum* cells. Many selectable marker genes may be used in connection with the present invention including, but not limited to the neo (neomycin resistance) gene which is selected for using G418 (Nellen, 1984), the bsr (blasticidin resistance) gene which is selected for using blasticidin (Sutoh, 1993), the hygromycin resistance gene (Egelhoff et al., 1989) which is selected for using hygromycin, the pyr 5–6 (UMP synthase) gene (Kalpaxis et al., 1991) with allows for the selection of uracil prototrophs from uracil auxotrophs, and the thymidylate synthase gene (Chang et al., 1989) which allows selection for thymidine prototrophs from thymidine auxotrophs. Further examples of selectable markers well known to one of skill in the art may be applicable.

C. Methods of Transformation

Suitable methods for nucleic acid delivery for transformation of a Dictyostelium cell for use with the current invention are electroporation or calcium phosphate precipitation.

i. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of *Dictyostelium discoideum* cells using electroporation is a routine procedure (Kuspa et al., 1992) in this manner.

ii. Calcium Phosphate

In other embodiments of the present invention, a nucleic acid is introduced to the cells using calcium phosphate precipitation. Transfection of *Dictyostelium discoideum* cells using calcium phosphate is a routine procedure (Nellen et al., 1984) in this manner.

7. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cell Growth and Maintenance

Standard methods for growth and maintenance of *Dictyostelium discoideum* will be used (Sussman, 1987). Cells of *Dictyostelium discoideum* strain capable of axenic growth (e.g., strain AX4) are cultured in HL-5 nutrient medium in shaken glass flasks where they divide exponentially. Cells are sub-cultured when they reach $3–5 \times 10^6$ cells per ml (stationary phase is $10^7$ cell per ml). For this invention, cells are used when they are between $2–5 \times 10^6$ cells per ml (log-phase). *Dictyostelium discoideum* cells are stored in liquid $N_2$ after suspending the cells in horse serum containing 5% dimethyl sulfoxide. They are viable under these conditions for at least 20 years. *Dictyostelium discoideum* cells that are stably transformed with reporter genes under the control of the repB, repD or APE promoters are grown, maintained and stored this way in identical fashion.

Example 2

Expression Assay

In one embodiment, equal aliquots of *Dictyostelium discoideum* strain AX4 cells ($10^6–10^7$) are removed from the culture (described above) and placed in multiwell plates. The agent being examined would be added to each of 2 wells for duplicate assay. Two additional control wells will receive an equal volume of the diluent used to dissolve the agent. After a set period of time the cells are removed from each well and an equal sample is taken for viability testing (see below). RNA is isolated from the remaining cells by well-known methods (Sambrook et al., 1989). These RNA samples are assayed for the levels of repB, repD and APE mRNA by the hybridization and detection methods described in detail earlier (section 5 above). In the case of Northern analysis, the samples could be slot-blotted onto a nylon support before hybridization. The levels of hybridization of the repB, repD and APE mRNAs in treated cells are compared to that in the parallel control untreated cells. They may increase, decrease or remain at basal levels.

In another embodiment, equal aliquots of *Dictyostelium discoideum* cultures which contain cells that stably transformed with a reporter gene under the control of the repB, repD or APE promoters (Section 6 above), are removed from the culture and placed in microtiter plates. The agent being examined would be added to each of 2 wells for duplicate assay. Two additional control wells will receive an equal volume of the diluent used to dissolve the agent. After a set period of time an equal sample of cells is removed from each well for viability testing (see below). The level of expression of the repB, repD and APE genes is measured in the remaining cells by adding the substrate for the reporter gene used (e.g., X-gal for a β-galactosidase reporter). The levels of β-galactosidase expression in the treated cells are compared to that in the parallel untreated cells. Again, they may increase, decrease or remain the same.

In initial assays, the effects on repB, repD and APE gene expression and on cytotoxcity of different concentrations of each agent and duration of the time of exposure to the agent may be detected.

Example 3

Cytotoxicity Assay

The cells that have been treated with the agent, as well as the control cells that are untreated, are serially diluted in isotonic buffer (e.g., 10-fold dilutions), equal aliquots are removed and each is plated on a nutrient agar plate in the presence of the bacteria *Klebsella aerogenes*, which forms a lawn over the plate. *Dictyostelium discoideum* cells phagocytize bacteria and use them as a food source. Thus, wherever there is a *Dictyostelium discoideum* cell on the plate, the bacteria are consumed and a clear plaque is formed due to continued mitotic division of the original cell. After 4 days, the plaques are counted as a measure of the number of viable cells at that dilution. The counts are corrected for dilution which provides a measure of viable cells in the cultures treated with and untreated with the agent, which in turn provides a direct measure of cytotoxicity (Sussman, 1987; Garcia et al., 2000).

Other methods including dye exclusion may be used as alternate or complementary methods for assessing cytotoxicity and are described in the literature (Garcia, 2000).

Example 4

Robotics

One embodiment employs liquid handling robots for most or all the steps including: dispensing the cells, adding agents, removing cells for viability testing (including making serial dilutions), preparing RNAs or assaying the reporter genes. In this configuration, thousands of agents are assayed per day, but even using manual methods hundreds of samples could be assayed per day.

8. References The following references, to the extent that they provide exemplary procedural or other details supplementary to those set forth herein, are specifically incorporated herein by reference.

U.S. Pat. No. 4,683,195
U.S. Pat. No. 4,883,750
U.S. Pat. No. 5,279,721
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,487
U.S. Pat. No. 5,849,497
U.S. Pat. No. 5,849,546
U.S. Pat. No. 5,849,547
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,384,253
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 4,683,202
U.S. Pat. No. 4,800,159
U.S. Pat. No. 5,849,486
U.S. Pat. No. 5,851,772
U.S. Pat. No. 5,900,481
U.S. Pat. No. 5,919,626

Broughton et al., *Am. J. Hum. Genet.,* 56:167–174, 1995.

Chang et al., "Complementation of a *Dictyostelium discoideum* thymidylate synthase mutation with the mouse gene provides a new selectable marker for transformation," *Nucl. Acids Res.* 17(10):3655–61, 1989.

Deering, R., "DNA repair in Dicytostelium," *Dev. Genet.* 9:483–493, 1988.

Drapkin et al., *Nature,* 368:769–772, 1994.

Egelhoff et al., "Hygromycin resistance as a selectable marker in *Dictyostelium discoideum,*" *Mol. Cell Biol.* 9(5):1965–8, 1989.

European Application No. 320 308
European Application No. 329 822

Freeland et al., "Apurinic/apyrimidinic (AP) endonuclease from *Dictyostelium discoideum*: cloning, nucleotide sequence and induction by sublethal levels of DNA damaging agents," *Nucl. Acid Res.* 24:1950–1953, 1996.

Friedberg et al., *DNA REPAIR AND MUTAGENESIS,* ASM Press, Washington, D.C., 1995.

Friedberg, *Annu. Rev. Biochem.,* 65:15–42, 1996.

Frohman, In. PCR PROTOCOLS. A GUIDE TO METHODS AND APPLICATIONS, Academic Press, N.Y., 1990.

Garcia et al., "Differential develomental expression and cell type specificity of Dictyostelium catalases and their response to oxidative stress and UV-light. *Biochim. Biophys. Acta* 1492:295–310, 2000.

GB Application No. 2 202 328

Gorbalenya and Koonin, *Curr. Biol.* 3:419–429, 1993.

Gulyas and Donahue, *Cell,* 69:1031–1042, 1992.

Guzder et al., *Nature,* 369:578–581, 1994.

Guzder et al., *J. Biol. Chem.,* 270:17660–17663, 1995.

Hanawalt and Mellon, *Curr. Biol.,* 3:67–69, 1993.

Hanawalt, *Science,* 266:1957–1958, 1994.

Higgins et al., *Proc. Nat'l Acad. Sci. USA,* 80:5680–5684, 1983.

Kalpaxis et al., "Positive selection for *Dictyostelium discoideum* mutants lacking UMP synthase activity based on resistance to 5-fluoroorotic acid," *Mol. Gen. Genet.* 225 (3):492–500, 1991.

Kessin, Dictyostelium: Evolution, Cell Biology and Development of Multicellularity, Cambridge University Press, Cambridge, UK and New York, 2000.

Kraemer et al., *J. Invest. Dermatol.,* 103:96S–101S, 1994.

Kuspa and Loomis, "Tagging developmental genes in Dictyostelium by restriction enzyme-mediated integration of plasmid DNA, *Proc. Nat'l Acad. Sci. USA* 89:8803–8807, 1992.

Kwoh et al., "Transcription-based amplification system and detection of amplified human immunodeficiency virus type 1 with a bead-based sandwich hybridization format," *Proc. Nat'l Acad. Sci.* USA 86(4):1173–1177, 1989.

Lee et al., *DNA Cell Biol,* 16(11):1267–1275, 1997.

Lee et al., *Nucl. Acids Res.* 25:2365–2374, 1997a.

Lee et al., *BioTechniques,* 21:630–632, 1996.

Lehmann, *Trends Biochem. Sci.,* 20:402–405, 1995.

Lohman and Bjornson, *Annu. Rev. Biochem.* 65:169–214, 1996.

Loomis, W., The Development of *Dictyostelium discoideum.* Academic Press, New York, 1982.

Nellen et al., "DNA-mediated transformation in *Dictyostelium discoideum*: regulated expression of an actin gene fusion," *Mol. Cell Biol.* 4(12):2890–8, 1984.

Ohara et al., "One-sided polymerase chain reaction: the amplification of cDNA," *Proc. Nat'l Acad. Sci. USA,* 86:5673–5677, 1989.

Park et al., *Proc. Nat'l Acad. Sci. USA,* 89:11461–11420, 1992.

PCT Application No. PCT/US87/00880

PCT Application No. PCT/US89/01025

PCT Application WO 88/10315

PCT Application WO 89/06700

PCT Application WO 90/07641

Potter et. al., *Proc. Nat'l Acad. Sci. USA,* 81:7161–7165, 1984.

Rhodes et al., "Transformation of maize by electroporation of embryos," *Methods Mol. Biol.,* 55:121–131, 1995.

Sambrook et al., In: *Molecular Cloning: A Laboratory Manual*, Vol. 1, Cold Spring Harbor Laboratory Press, Cold Spring Harbor, N.Y., Ch. 7,7.19–17.29, 1989.

Sancar, *Annu. Rev. Biochem.,* 65:43–81, 1996.

Sussman, M., "Cultivation and synchronus morphogenesis of Dictyostelium under controlled experimental conditions, *Meth. Cell Biol.* 28:9–29, 1987.

Sutoh, K., "A transformation vector for *Dictyostelium discoideum* with a new selectable marker bsr," *Plasmid* 30(2):150–4, 1993.

Svejstrup et al., *Cell,* 80:21–28, 1995.

Sweder and Hanawalt, *J. Biol. Chem.,* 269:1852–1857, 1994.

Takayama et al., *Cancer Res.,* 55:5656–5663, 1995.

Tsukada et al., *Plant Cell Physiol.,* 30(4)599–604, 1989.

Van Vuuren et al., *EMBO J.,* 13:1645–1653, 1994.

Walker et al., "Strand displacement amplification—an isothermal, in vitro DNA amplification technique," *Nucleic Acids Res.* 20(7):1691–1696, 1992.

WO Application No. 9217598

Yu et al., "Rapid changes of Nucleotide excision repair gene expression following UV-irradiation and cisplatin treatment Of *Dictyostelium Discoideum*," *Nucl. Acids Res.,* 26:3397–3403, 1998.

Zhou et al., "Adeno-associated virus 2 mediated gene transfer in murine hematopoietic cells, *Exp. Hematol* 21:928–933, 1993.

What is claimed is:

1. A method of screening and classifying agents based on cytotoxicity in *Dictyostelium discoideum* comprising first screening by:
   (a) contacting a vegetative cell of *Dictyostelium discoideum* with a test agent;
   (b) assessing the cytotoxicity of said test agent;
   (c) assessing the effect of said test agent on the expression of one or more of repB, repD and APE gene products; and
   (d) comparing said cytotoxicity and said expression in the presence of said test agent with a vegetative cell of *Dictyostelium discoideum* not exposed to said test agent;

and then classifying as:
   (i) a test agent that is cytotoxic but does not induce expression of one or more of repB, repD and APE gene products;
   (ii) a test agent that is not cytotoxic but does induce expression of one or more of repB, repD and APE gene products; or
   (iii) a test agent that inhibits the expression of one or more of repB, repD and APE gene products.

2. The method of claim 1, wherein assessing expression of repB is performed, and assessing expression of repD and APE is not performed.

3. The method of claim 1, wherein assessing expression of repD is performed, and assessing expression of repB and APE is not performed.

4. The method of claim 1, wherein assessing expression of APE is performed, and assessing expression of repB and repD is not performed.

5. The method of claim 1, wherein assessing expression of repB and repD is performed, and assessing expression of APE is not performed.

6. The method of claim 1, wherein assessing expression of repB and APE is performed, and assessing expression of repD is not performed.

7. The method of claim 1, wherein assessing expression of repD and APE is performed, and assessing expression of repB is not performed.

8. The method of claim 1, wherein assessing expression of repB, repD and APE is performed.

9. The method of claim 1, further comprising measuring, in a vegetative cell of *Dictyostelium discoideum* not treated with said test agent, the expression of the same gene or genes as measured in step (c).

10. The method of claim 1, wherein cytoxocity is assessed by measuring clonal plating, trypan blue exclusion, phyloxine B dye exclusion, and degradation/laddering of DNA.

11. The method of claim 1, wherein expression is assessed by hybridization of a probe to a target nucleic acid.

12. The method of claim 11, further comprising RT-PCR™.

13. The method of claim 12, wherein said probe is a member of a primer pair for RT-PCR™ and comprises a label.

14. The method of claim 13, wherein the label is a radiolabel, a fluorophore label, a chemilluminescent label, an enzyme label or a ligand.

15. The method of claim 14, wherein the ligand is biotin, and the ligand is detected by contacting with enzyme-conjugated avidin and a detectable enzyme substrate.

16. The method of claim 11, further comprising binding target nucleic acid to a substrate.

17. The method of claim 16, wherein said substrate is a nylon or nitrocellulose membrane.

18. The method of claim 16, wherein said probe is labeled with a radiolabel, a fluorophore label, a chemilluminescent label, an enzyme label or a ligand.

19. The method of claim 1, wherein expression is assessed by means of an expression cassette stably transformed into said a vegetative cell of *Dictyostelium discoideum*, said expression cassette comprising a nucleic acid segment encoding a detectable reporter enzyme under the transcriptional control of a repB, repD or APE promoter region.

20. The method of claim 19, wherein said detectable reporter enzyme encodes β-galactosidase, β-glucuronidase, luciferase or green fluorescent protein.

21. The method of claim 1, wherein said assay further comprises a positive control for inhibition of expression of one or more of repB, repD and APE gene products.

22. The method of claim 1, wherein said assay further comprises a positive control for induction of expression of one or more of repB, repD and APE gene products.

23. The method of claim 1, wherein said assay further comprises a positive control for cytotoxicity.

24. The method of claim 1, wherein said assay further comprises a negative control for inhibition of expression of one or more of repB, repD and APE gene products.

25. The method of claim 1, wherein said assay further comprises a negative control for induction of expression of one or more of repB, repD and APE gene products.

26. The method of claim 1, wherein said assay further comprises a negative control for cytotoxicity.

27. The method of claim 1, wherein said test agent is a naturally-occurring molecule.

28. The method of claim 1, wherein said test agent is a synthetic molecule.

29. The method of claim 1, wherein said test agent is a synthetic derivative of a naturally-occurring molecule.

30. The method of claim 1, further comprising assessing DNA damage in said cell.

31. The method of claim 30, wherein assessing DNA damage comprising mass spectroscopy.

* * * * *

UNITED STATES PATENT AND TRADEMARK OFFICE
CERTIFICATE OF CORRECTION

PATENT NO. : 6,746,843 B2  Page 1 of 1
DATED : June 8, 2004
INVENTOR(S) : Hannah Alexander et al.

It is certified that error appears in the above-identified patent and that said Letters Patent is hereby corrected as shown below:

Column 18,
Line 58, delete "said a" and insert -- said -- therefor.

Column 20,
Line 11, delete "comprising" and insert -- comprises -- therefor.

Signed and Sealed this

Nineteenth Day of April, 2005

JON W. DUDAS
*Director of the United States Patent and Trademark Office*